(12) United States Patent  
Buchmann et al.

(10) Patent No.: US 7,417,066 B2  
(45) Date of Patent: Aug. 26, 2008

(54) INHIBITORS OF SOLUBLE ADENYLATE CYCLASE

(75) Inventors: Bernd Buchmann, Hohen Neuendorf (DE); Martin Fritsch, Berlin (DE); Duy Nguyen, Berlin (DE); Bernd Menzenbach, Jena (DE); Ulf Boemer, Glienicke/Nordbahn (DE)

(73) Assignee: Schering AG, Berlin (DE)

( * ) Notice: Subject to any disclaimer, the term of this patent is extended or adjusted under 35 U.S.C. 154(b) by 157 days.

(21) Appl. No.: 11/448,140

(22) Filed: Jun. 7, 2006

(65) Prior Publication Data

US 2006/0281744 A1 Dec. 14, 2006

Related U.S. Application Data

(60) Provisional application No. 60/691,776, filed on Jun. 20, 2005.

(30) Foreign Application Priority Data

Jun. 8, 2005 (DE) ............... 10 2005 027 274

(51) Int. Cl.
  *A01N 43/12* (2006.01)
  *A01N 43/40* (2006.01)
  *A61K 31/497* (2006.01)
  *A61K 31/535* (2006.01)
  *C07D 333/72* (2006.01)
  *C07D 333/00* (2006.01)
  *C07D 307/00* (2006.01)

(52) U.S. Cl. ............... 514/443; 514/232.5; 514/252.13; 514/337; 549/55; 549/57; 549/468

(58) Field of Classification Search ............ 549/55, 549/57, 468; 544/376, 145; 514/232.5
See application file for complete search history.

(56) References Cited

U.S. PATENT DOCUMENTS

2006/0074084 A1  4/2006  Nguyen et al.

FOREIGN PATENT DOCUMENTS

| DE | 10 2004047272 A1 | 4/2006 |
|---|---|---|
| FR | 2 635 776 A1 | 3/1990 |
| WO | WO 02/20745 A1 | 3/2002 |
| WO | WO 03/002533 A1 | 1/2003 |
| WO | WO 03/024448 A2 | 3/2003 |
| WO | WO 2004/041782 A | 5/2004 |
| WO | WO 2005/013996 A2 | 2/2005 |
| WO | WO 2005/034880 A2 | 4/2005 |
| WO | WO 2005/070419 A1 | 8/2005 |
| WO | WO 2005/092899 A1 | 10/2005 |

*Primary Examiner*—Janet L. Andres
*Assistant Examiner*—Kristin Bianchi
(74) *Attorney, Agent, or Firm*—Millen, White, Zelano & Branigan, P.C.

(57) ABSTRACT

The invention relates to compounds of general Formula I, the production thereof, and the use thereof as a medicinal product.

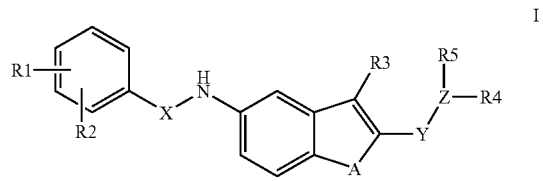

15 Claims, No Drawings

INHIBITORS OF SOLUBLE ADENYLATE CYCLASE

This application claims the benefit of the filing date of U.S. Provisional Application Ser. No. 60/691,776 filed Jun. 20, 2005.

The present invention relates to inhibitors of soluble adenylate cyclase, production thereof and use thereof for the production of a medicinal product for contraception.

A large number of modern methods of contraception are currently available for women, but very few methods are available for male fertility control (condom and sterilization). Development of reliable new means of male fertility control is urgently needed. The infertility brought about by a "male pill" should be reversible and should be just as effective as the existing methods available to women. Infertility should be developed relatively quickly and should persist for as long as possible. Such a method of contraception should have no side-effects, and the preparations may be non-hormonal as well as hormonal. A possible starting point is regulation of the activity of an enzyme that plays an important role in fertilization of the ovum: soluble adenylate cyclase (sAC). This enzyme is mainly expressed in the testicular stem cells and is present in mature sperm.

In 1999, the authors Levin and Buck succeeded in purifying and cloning an isoform of sAC from rat testes (Proc. Natl. Acad. Sci. USA 96 (1): 79-84).

The recombinant rat enzyme can be stimulated by bicarbonate. It was demonstrated, using antibodies, that the catalytic domain of the enzyme is localized in testes, sperm, kidneys and the choroid plexus. These disclosures are the subject of application WO01/85753, which was granted in the USA (U.S. pat. No. 6,544,768).

WO01/21829 (Conti et al.) claims isolated polynucleotide sequences that code for the human isoform of sAC, isolated sAC polypeptides and test systems, using which it is possible to identify substances that inhibit the activity of sAC. The possibility of using these substances to achieve a reversible reduction in the motile sperm count, and their use as a means of controlling male fertility, is disclosed.

John Herr's group demonstrated the isolation and characterization of the human isoform of sAC from sperm. WO 02/20745 claims, in addition to nucleic acids that code for sAC, also test systems for identifying substances that modulate the expression or the activity of human sAC. Such compounds might, for example, selectively inhibit the activity of sAC, as a consequence of which the sperm would lose the capacity to fertilize an ovum. These sAC inhibitors might therefore serve as medicinal products for non-hormonal contraception.

However, the sAC inhibitors that are already known display specific problems: catechol estrogens (T. Braun, Proc Soc Exp Biol Med 1990, 194(1): 58ff) and gossypol (KL Olgiati, Arch Biochem Biophys 1984, 231(2): 411ff) are inherently toxic, whereas adenosine analogs only have a very weak inhibitory action (MA Brown and ER Casillas, J Androl 1984, 5:361ff). The inhibitors of recombinant human sAC described by Zippin et al. are somewhat more potent ($IC_{50} \leq 10$ μM) (JH Zippin et al., J Cell Biol 2004, 164(4): 527ff).

In order to provide a means for male fertility control, there is an increasing demand for substances that lead to infertility quickly, reversibly and successfully.

This problem is solved by the provision of the compounds of general Formula I,

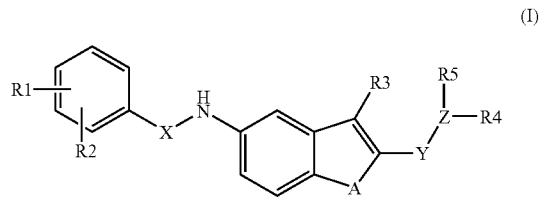

where the following notation is used:

$R^1$ a hydrogen, halogen, $CF_3$, a $C_3$-$C_6$-cycloalkyl, which is optionally multiply saturated and optionally multiply substituted, or the group $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, $C_1$-$C_6$-aryl-$C_1$-$C_6$-alkyl or $CF_3$, in which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-C6-aryl or $C_1$-$C_6$-aryl-$C_1$-$C_6$-alkyl can optionally be interrupted singly or multiply, identically or differently by oxygen, sulfur or nitrogen, or the group sulfonyl-$C_1$-$C_6$-alkyl, sulfonamide, or cyano, $R^2$ a halogen, $CF_3$, a $C_3$-$C_6$-cycloalkyl, which is optionally multiply saturated and optionally multiply substituted, or the group $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, $C_1$-$C_6$-aryl-$C_1$-$C_6$-alkyl or $CF_3$, in which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl or $C_1$-$C_6$-aryl-$C_1$-C6-alkyl can optionally be interrupted singly or multiply, identically or differently by oxygen, sulfur or nitrogen, or the group sulfonyl-$C_1$-$C_6$-alkyl, sulfonamide, or cyano, $R^3$ a $C_6$-$C_{12}$-aryl, which can optionally be substituted singly or multiply, identically or differently with halogen, with $C_1$-$C_6$-alkyl or $C_1$-$C_6$-acyl, which can optionally be singly or multiply substituted, or can be substituted with $C_1$-$C_6$-alkoxy, hydroxy, cyano, $CO_2$-($C_1$-$C_6$-alkyl), N—($C_1$-$C_6$-alkyl)$_2$, CO—$NR^4R^5$ or with $CF_3$, a $C_5$-$C_{12}$-heteroaryl, which can optionally be substituted singly or multiply, identically or differently with halogen, with $C_1$-$C_6$-alkyl, $C_1$-$C_6$-acyl, $C_1$-$C_6$-alkoxy, hydroxy, cyano, $CO_2$-($C_1$-$C_6$-alkyl), N—($C_1$-$C_6$-alkyl)$_2$, CO—$NR^4R^5$ or with $CF_3$ or a $C_3$-$C_6$-cycloalkyl, which can optionally be substituted singly or multiply, identically or differently with halogen, $CF_3$, hydroxy, cyano, $CO_2$—($C_1$-$C_6$-alkyl), $C_1$-$C_6$-alkyl, $C_1$-$C_6$-acyl, N—($C_1$-$C_6$-alkyl)$_2$, CO—$NR^4R^5$ or $C_1$-$C_6$-alkoxy, $R^4$ a hydrogen, a $C_3$-$C_6$-cycloalkyl, which is optionally substituted singly or multiply, identically or differently with $C_1$-$C_6$-alkyl, $C_1$-$C_6$-acyl, $C_1$-$C_6$-alkoxy or $CF_3$, a $C_6$-$C_{12}$-aryl, which is optionally substituted singly or multiply, identically or differently with halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano, or a $C_5$-$C_{12}$-heteroaryl, which is optionally substituted singly or multiply, identically or differently with halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano, or a $C_1$-$C_6$-alkyl, which can be substituted arbitrarily, $R^5$ a hydrogen, a $C_3$-$C_6$-cycloalkyl, which is optionally substituted singly or multiply, identically or differently with $C_1$-$C_6$-alkyl, $C_1$-$C_6$-acyl, $C_1$-$C_6$-alkoxy or $CF_3$, a $C_6$-$C_{12}$-aryl, which is optionally substituted singly or multiply, identically or differently with halogen, with $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano, or a $C_5$-$C_{12}$-heteroaryl, which is optionally substituted singly or multiply, identically or differently with halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano, or a $C_1$-$C_6$-alkyl, which can be substituted arbitrarily, $R^4$ and $R^5$ together form a 5-8-membered ring, which can contain further heteroatoms, and X the groups sulfonyl, $(CH_2)_n$ or carbonyl, Y a —$(CH_2)_n$— or carbonyl group Z a nitrogen, A an oxygen or sulfur and n 0-4, as well as their isomers, diastereomers, enantiomers and salts, which overcome the known drawbacks and display improved properties, i.e. display good efficacy, good solubility and stability.

The compounds according to the invention inhibit soluble adenylate cyclase and so prevent capacitation of the sperm and thus provide male fertility control.

Alkyl means in each case a linear or branched alkyl residue, such as methyl, ethyl, propyl, isopropyl, butyl, isobutyl, sec. butyl, tert. butyl, pentyl, isopentyl and hexyl.

Alkoxy means in each case a linear or branched alkoxy residue, such as methoxy-, ethoxy-, n-propoxy-, iso-propoxy-, n-butoxy-, sec-butoxy-, iso-butoxy-, tert. butyloxy-, pentoxy-, iso-pentoxy- and hexoxy-.

Acyl means in each case a linear or branched residue, such as formyl, acetyl, propionyl, butyroyl, iso-butyroyl, valeroyl and benzoyl.

Cycloalkyl means monocyclic alkyl rings such as cyclopropyl, cyclobutyl, cyclopentyl and cyclohexyl.

The cycloalkyl residues can contain one or more heteroatoms, such as oxygen, sulfur and/or nitrogen, instead of the carbon atoms. Such heterocycloalkyls with 3 to 6 ring atoms are preferred. The ring systems, in which optionally one or more possible double bonds can be contained in the ring, mean for example cycloalkenyls such as cyclopropenyl, cyclobutenyl, cyclopentenyl, cyclopentadienyl, cyclohexenyl, cycloheptenyl, where the coupling can take place both on the double bond and on the single bonds.

Halogen means in each case fluorine, chlorine, bromine or iodine.

In each case the aryl residue comprises 6-12 carbon atoms and can for example be benzocondensed. The following may be mentioned as examples: phenyl, tropyl, cyclooctadienyl, indenyl, naphthyl, biphenyl, florenyl, anthracenyl etc.

In each case the heteroaryl residue comprises 5-16 ring atoms and can contain one or more, identical or different heteroatoms, such as oxygen, sulfur or nitrogen in the ring instead of carbon, and can be mono-, bi- or tricyclic and can additionally be benzocondensed in each case.

The following may be mentioned as examples: thienyl, furanyl, pyrrolyl, oxazolyl, imidazolyl, pyrazolyl, isoxazolyl, isothiazolyl, oxadiazolyl, triazolyl, thiadiazolyl, etc. and benzo derivatives thereof, e.g. benzofuranyl, benzothienyl, benzooxazolyl, benzimidazolyl, indazolyl, indolyl, isoindolyl, etc; or pyridazinyl, pyrimidinyl, pyrazinyl, triazinyl, etc. and benzo derivatives thereof, e.g. quinolyl, isoquinolyl, etc; or azozinyl, indolizinyl, purinyl, etc. and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, oxepinyl, etc.

The heteroaryl residue can be benzocondensed in each case. For example, the following may be mentioned as 5-ring heteroaromatics: thiophene, furan, oxazole, thiazole, imidazole, pyrazole and benzo derivatives thereof and as 6-ring-heteroaromatics pyridine, pyrimidine, triazine, quinoline, isoquinoline and benzo derivatives.

Heteroatoms is to be taken to mean oxygen, nitrogen or sulfur atoms.

If an acid function is present, the physiologically compatible salts of organic and inorganic bases are suitable as salts, such as the readily soluble alkali and alkaline-earth salts and N-methyl-glucamine, dimethyl-glucamine, ethyl-glucamine, lysine, 1,6-hexadiamine, ethanolamine, glucosamine, sarcosine, serinol, tris-hydroxymethylaminomethane, aminopropanediol, Sovak base, 1-amino-2,3,4-butanetriol.

If a basic function is present, the physiologically compatible salts of organic and inorganic acids are suitable, such as hydrochloric acid, sulfuric acid, phosphoric acid, citric acid, tartaric acid etc.

Compounds of general Formula I in which the symbols have the following meanings are especially preferred, $R^1$ a hydrogen, halogen, $CF_3$, a $C_3$-$C_6$-cycloalkyl, or the group $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, $C_1$-$C_6$-aryl-$C_1$-$C_6$-alkyl or $CF_3$, in which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl or $C_1$-$C_6$-aryl-$C_1$-$C_6$-alkyl can optionally be interrupted singly or multiply, identically or differently by oxygen, sulfur or nitrogen, or the group sulfonyl-$C_1$-$C_6$-alkyl, sulfonamide, or cyano, $R^2$ a halogen, $CF_3$, a $C_3$-$C_6$-cycloalkyl, or the group $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, $C_1$-$C_6$-aryl-$C_1$-$C_6$-alkyl or $CF_3$, in which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl or $C_1$-$C_6$-aryl-$C_1$-$C_6$-alkyl can optionally be interrupted singly or multiply, identically or differently by oxygen, sulfur or nitrogen, or the group sulfonyl-$C_1$-$C_6$-alkyl, sulfonamide, or cyano, $R^3$ a $C_6$-$C_{12}$-aryl, which can optionally be substituted singly or multiply, identically or differently with halogen, with $C_1$-$C_6$-alkyl, $C_1$-$C_3$-acyl, $C_1$-$C_3$-alkoxy, cyano, hydroxy, N—$(CH_3)_2$, $CO_2$—$(C_1$-$C_3$-alkyl), CO—$NR^4R^5$ or with $CF_3$, a $C_5$-$C_{12}$-heteroaryl, which can optionally be substituted singly or multiply, identically or differently with chlorine and/or fluorine, with $C_1$-$C_6$-alkyl, $C_1$-$C_3$-acyl, $C_1$-$C_3$-alkoxy, cyano, hydroxy, N—$(CH_3)_2$, $CO_2$—$(C_1$-$C_3$-alkyl), CO—$NR^4R^5$ or with $CF_3$, a $C_3$-$C_6$-cycloalkyl, which can optionally be substituted singly or multiply, identically or differently with chlorine and/or fluorine, $CF_3$, cyano, $C_1$-$C_3$-alkyl, $C_1$-$C_3$-acyl, hydroxy, N—$(CH_3)_2$, $CO_2$—$(C_1$-$C_3$-alkyl), CO—$NR^4R^5$ or $C_1$-$C_3$-alkoxy, $R^4$ a hydrogen, a $C_3$-$C_6$-cycloalkyl, which is optionally substituted singly or multiply, identically or differently with $C_1$-$C_3$-alkyl, $C_1$-$C_3$-acyl, $C_1$-$C_3$-alkoxy or $CF_3$, a $C_6$-$C_{12}$-aryl, which is optionally substituted singly or multiply, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or a $C_5$-$C_{12}$-heteroaryl, which is optionally substituted singly or multiply, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or a $C_1$-$C_6$-alkyl, which can be substituted arbitrarily, $R^5$ a hydrogen, a $C_3$-$C_6$-cycloalkyl, which is optionally substituted singly or multiply, identically or differently with $C_1$-$C_3$-alkyl, $C_1$-$C_3$-acyl, $C_1$-$C_3$-alkoxy or $CF_3$, a $C_6$-$C_{12}$-aryl, which is optionally substituted singly or multiply, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or a $C_5$-$C_{12}$-heteroaryl, which is optionally substituted singly or multiply, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or a $C_1$-$C_6$-alkyl, which can be substituted arbitrarily, $R^4$ and $R^5$ together form a 5-8-membered ring, which can contain further heteroatoms, and x the groups sulfonyl, $(CH_2)_n$ or carbonyl, Y a —$(CH_2)_n$— or carbonyl group, Z a nitrogen, A an oxygen or sulfur, and n stands for 0-2, as well as their isomers, diastereomers, enantiomers and salts.

Compounds of general Formula I in which the symbols have the following meanings are also preferred, $R^1$ a hydrogen, $R^2$ a $C_3$-$C_6$-cycloalkyl, $C_1$-$C_6$-alkyl, $CF_3$, cyano, bromine, or the group —$OCF_3$, —$SO_2$—$CH_3$, $R^3$ a $C_6$-$C_{12}$-aryl, which can optionally be substituted singly or multiply, identically or differently with halogen, $C_1$-$C_6$-alkyl, $C_1$-$C_3$-acyl, $C_1$-$C_3$-alkoxy, cyano, hydroxy, N—$(CH_3)_2$, $CO_2$-$(C_1$-$C_3$-alkyl), CO—$NR^4R^5$ or $CF_3$, a $C_5$-$C_{12}$-heteroaryl, which can optionally be substituted singly or multiply, identically or differently with chlorine and/or fluorine, with $C_1$-$C_6$-alkyl, $C_1$-$C_3$-acyl, $C_1$-$C_3$-alkoxy, cyano, hydroxy, N—$(CH_3)_2$, $CO_2$—$(C_1$-$C_3$-alkyl), CO—$NR^4R^5$ or with $CF_3$, a $C_3$-$C_6$-cycloalkyl, which can optionally be substituted singly or multiply, identically or differently with chlorine and/or fluorine, $CF_3$, cyano, $C_1$-$C_3$-alkyl, $C_1$-$C_3$-acyl, hydroxy, N—$(CH_3)_2$, $CO_2$—$(C_1$-$C_3$-alkyl), CO—$NR^4R^5$ or $C_1$-$C_3$-alkoxy, $R^4$ a hydrogen, a $C_3$-$C_6$-cycloalkyl, which is optionally substituted singly or multiply, identically or differently with $C_1$-$C_3$-alkyl, $C_1$-$C_3$-acyl, $C_1$-$C_3$-alkoxy or $CF_3$, a $C_6$-$C_{12}$-aryl, which is optionally substituted singly or multiply, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or a $C_5$-$C_{12}$-heteroaryl, which is optionally substituted singly or multiply, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or a $C_1$-$C_6$-alkyl, which can be substituted arbitrarily, $R^5$ a hydrogen, X a sulfonyl or carbonyl group or —$(CH_2)_n$, Y a —$(CH_2)_n$— or carbonyl group, Z a nitrogen, A an oxygen or sulfur and n 0-2 as well as their isomers, diastereomers, enantiomers and salts.

Compounds of general Formula I in which the symbols have the following meanings are also preferred, $R^1$ a hydrogen, $R^2$ a $C_3$-$C_6$-cycloalkyl, $C_1$-$C_6$-alkyl, $CF_3$, cyano, bromine, or the group —$OCF_3$, —$SO_2$-$CH_3$ in the para-position, $R^3$ a $C_6$-$C_{12}$-aryl, which can optionally be substituted singly or doubly, identically or differently with halogen, $C_1$-$C_3$-alkyl, acetyl, methoxy, ethoxy, cyano, hydroxy, N—$(CH_3)_2$, $CO_2$—$(C_1$-$C_3$-alkyl), CO—$NHR^5$ or $CF_3$, a $C_5$-$C_{12}$-heteroaryl, which can optionally be substituted singly or doubly, identically or differently with chlorine and/or fluorine, with $C_1$-$C_3$-alkyl, acetyl, methoxy, ethoxy, cyano, hydroxy, N—$(CH_3)_2$, $CO_2$—$(C_1$-$C_3$-alkyl), CO—$NHR^5$ or with $CF_3$, a $C_3$-$C_6$-cycloalkyl, $R^4$ a hydrogen, a $C_3$-$C_6$-cycloalkyl, which is optionally substituted singly or multiply, identically or differently with $C_1$-$C_3$-alkyl, $C_1$-$C_3$-acyl, $C_1$-$C_3$-alkoxy or $CF_3$, a $C_6$-$C_{12}$-aryl, which is optionally substituted singly or multiply, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or a $C_5$-$C_{12}$-heteroaryl, which is optionally substituted singly or multiply, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or a $C_1$-$C_6$-alkyl, which can be substituted arbitrarily, $R^5$ a hydrogen, X a sulfonyl or carbonyl group or —$(CH_2)_n$, Y a —$(CH_2)_n$— or carbonyl group, Z a nitrogen, A an oxygen or sulfur and n 1-2 as well as their isomers, diastereomers, enantiomers and salts.

Compounds of general Formula I in which the symbols have the following meanings are also preferred, $R^1$ a hydrogen, $R^2$ a tertiary butyl, iso-propyl, iso-butyl, sec. butyl, cyano, bromine, or the group —O—$CF_3$, —$SO_2$-$CH_3$ in the para-position, R³ the group

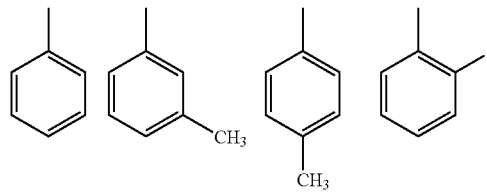

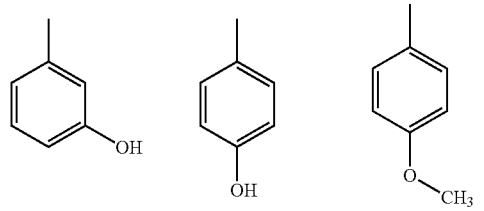

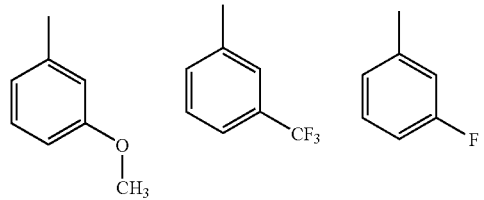

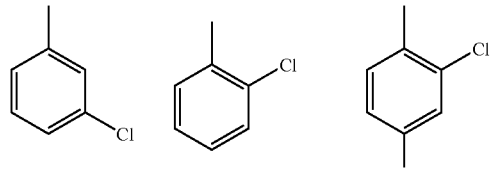

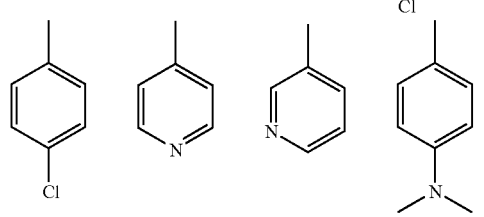

R⁴ a hydrogen or the group —(CH₂)ₙ—N—(CH₃)₂, —(CH₂)₂—CH₃, —(CH₂)₂—NH—COCH₃, —(CH₂)—CHCH₃—OH, —(CH₂)₂—O—CH₃, —(CH₂)₂—OH, —CHCH₃-CH₂—OH, —(CH₂)₃—C(CH₃)₂—CH₂—OH, —CH₂—CN,

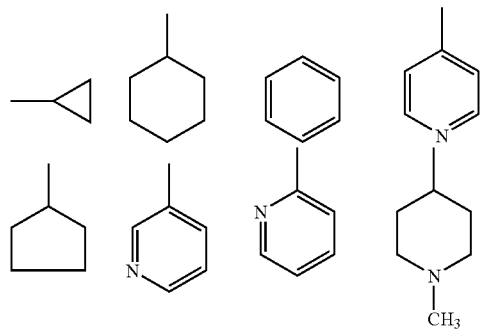

-continued

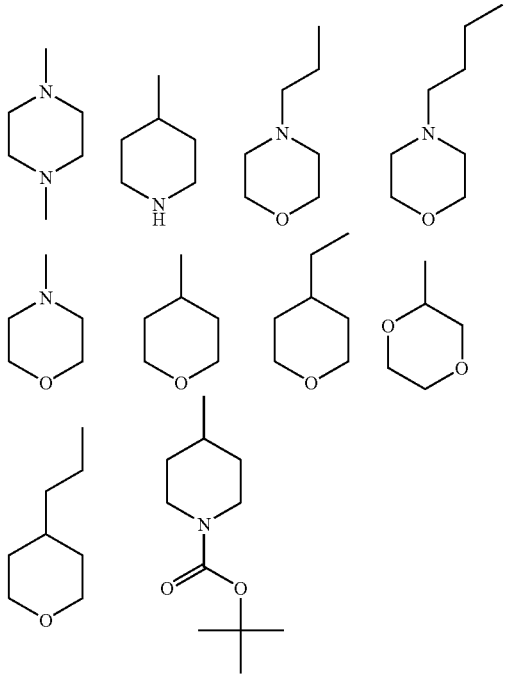

R⁵ a hydrogen,
X a sulfonyl or carbonyl group or —(CH₂)ₙ,
Y a —(CH₂)ₙ— or carbonyl group,
Z a nitrogen,
A an oxygen or sulfur and
n 1-2 as well as their isomers, diastereomers, enantiomers and salts.

Compounds of general Formula I in which the symbols have the following meanings are also preferred, R¹ a hydrogen,
R² a tertiary butyl, iso-propyl, iso-butyl, sec. butyl, cyano, bromine, or the group —O—CF₃, —SO₂—CH₃ in the para-position,
R³ the group

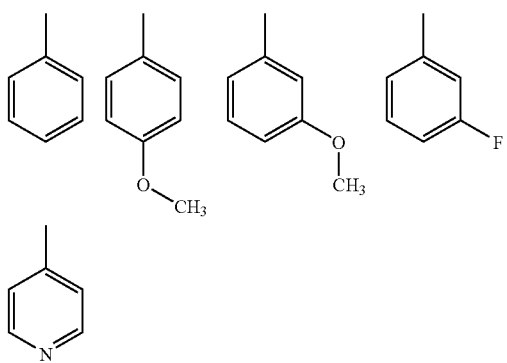

R⁴ hydrogen or the group, —(CH₂)—CHCH₃—OH, —(CH₂)₂—O—CH₃, —CHCH₃—CH₂—OH, , —(CH₂)₃—CH(CH₃)₂—CH₂—OH, —CH₂—CN,

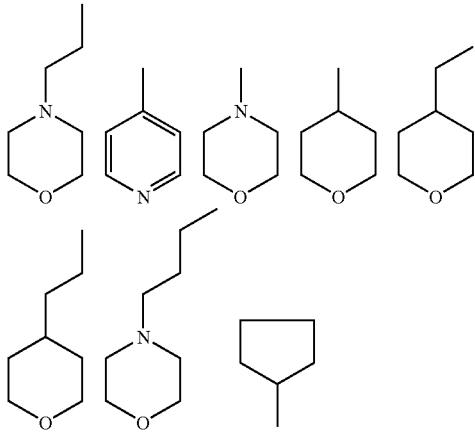

5 hydrogen,
X a sulfonyl or carbonyl group, or —(CH$_2$)$_n$—
Y a —(CH$_2$)$_n$— or carbonyl group,
Z a nitrogen,
A an oxygen or sulfur and
n 1-2 as well as their isomers, diastereomers, enantiomers and salts.

The following compounds according to the present invention are quite especially preferred:

- (+/−)-5-(4-tert-Butylbenzenesulfonylamino)-3-phenyl-1-benzothiophene-2-carboxylic acid-(2-hydroxypropyl)amide
- (+/−)-5-(4-tert-Butylbenzenesulfonylamino)-3-phenyl-1-benzothiophene-2-carboxylic acid-(2-hydroxymethyl-ethyl)amide
- 5-(4-tert-Butylbenzenesulfonylamino)-3-phenyl-1-benzothiophene-2-carboxylic acid-(tetrahydropyran-4-yl)amide
- 5-(4-tert-Butylbenzenesulfonylamino)-3-phenyl-1-benzothiophene-2-carboxylic acid-(2-morpholin-4-yl-ethyl)amide
- 5-(4-tert-Butylbenzenesulfonylamino)-3-phenyl-1-benzofuran-2-carboxylic acid-(tetrahydropyran-4-yl)amide
- 5-(4-tert-Butylbenzenesulfonylamino)-3-phenyl-1-benzofuran-2-carboxylic acid-(2-morpholin-4-yl-ethyl)amide
- 5-(4-tert-Butyl-phenylsulfonylamino)-3-phenyl-benzo[b]thiophene-2-carboxylic acid-(3-morpholin-4-yl-propyl)-amide
- 5-(4-tert-Butyl-phenylsulfonylamino)-3-phenyl-benzo[b]thiophene-2-carboxylic acid-cyclopentyl-amide
- 5-(4-tert-Butyl-phenylsulfonylamino)-3-phenyl-benzo[b]thiophene-2-carboxylic acid-(4-pyridyl)-amide
- 5-(4-tert-Butyl-phenylsulfonylamino)-3-phenyl-benzo[b]thiophene-2-carboxylic acid-(2-methoxy-ethyl)-amide
- 5-(4-tert-Butyl-phenylsulfonylamino)-3-phenyl-benzo[b]thiophene-2-carboxylic acid-cyclohexyl-amide
- 5-(4-tert-Butyl-phenylsulfonylamino)-3-phenyl-benzo[b]thiophene-2-carboxylic acid-(2-hyxdroxy-ethyl)-amide
- 5-(4-tert-Butyl-phenylsulfonylamino)-3-phenyl-benzo[b]thiophene-2-carboxylic acid-(2-propen-1-yl)-amide
- 5-(4-tert-Butyl-phenylsulfonylamino)-3-phenyl-benzo[b]thiophene-2-carboxylic acid-(2-acetylamino-ethyl)-amide
- 5-(4-tert-Butyl-phenylsulfonylamino)-3-phenyl-benzo[b]thiophene-2-carboxylic acid-(5-hydroxy-4,4-dimethyl-pentyl)-amide
- (+/−)-5-(4-tert-Butylphenylsulfonylamino)-3-phenyl-1-benzofuran-2-carboxylic acid-(2-hydroxypropyl)amide
- (+/−)-5-(4-tert-Butylbenzenesulfonylamino)-3-phenyl-1-benzofuran-2-carboxylic acid-(2-hydroxy-1-methyl-ethyl)amide.

The compounds according to the invention inhibit soluble adenylate cyclase, and this is also the basis of their action for example in male fertility control.

Adenylate cyclases are the effector molecules for one of the most-used signal-transduction pathways, they synthesize the second messenger molecule cyclic adenosine monophosphate (cAMP) from adenosine triphosphate (ATP) with splitting-off of pyrophosphate (PP). cAMP mediates numerous cellular responses to a large number of neurotransmitters and hormones. Soluble, sperm-specific adenylate cyclase (sAC, human mRNA sequence (GenBank) nm_018417, human gene ADCY X) is one out of ten adenylate cyclases described in the human genome. sAC exhibits some specific properties that distinguish it from the other adenylate cyclases. In contrast to all other adenylate cyclases, sAC is stimulated by the concentration of bicarbonate in the surrounding medium and not by G proteins. sAC does not possess any transmembrane regions in its amino acid sequence, it cannot be inhibited by forskolin, can be stimulated much more strongly by manganese than by magnesium, and only displays slight sequence homologies to the other adenylate cyclases (≦26% identity of the catalytic domains I and II of sAC with other adenylate cyclases at the amino acid level).

Specific, manganese-dependent activity of sAC was first described by T. Braun et al. (175, PNAS 73:107ff) in rat testis and sperm. N. Okamura et al. (185, J. Biol. Chem 260(17): 6ff) showed that the substance which stimulates the activity of sAC in boar seminal fluid is bicarbonate. It was also shown that AC activity that can be stimulated by bicarbonate can only be detected in rat testis and sperm, but not in other tissues. sAC was purified from rat testis and sequenced for the first time by the Buck and Levin group (J. Buck et al. 1, PNAS 6:7ff, WO 01/85753). The expected properties (e.g. capacity to be stimulated by bicarbonate and magnesium) were confirmed on recombinantly expressed protein (Y. Chen et al. 2000, Science 28:625ff).

Testis-specific and sperm-specific expression of the enzymes can be concluded from data on the distribution of sAC mRNA and on sAC activity that can be stimulated by bicarbonate (ML Sinclair et al. 2000, Mol Reprod Develop 56:6ff; N Okamura et al. 185, J. Biol. Chem 260(17):9699ff; J. Buck et al. 1999, PNAS 96:79ff). In the testis, sAC mRNA is only expressed in later stages, of the gametes developing to sperm, but not in somatic cells (ML Sinclair et al. 2000, Mol Reprod Develop 56:6ff).

There have been a number of pharmacological investigations into the function of sAC in sperm in mammals. Before sperm can penetrate the zona pellucida of the ovum and then fuse with the oolemma of the ovum, sperm must be prepared for this functionality. This process, sperm capacitation, has been thoroughly investigated. A capacitated sperm is characterized by an altered pattern of movement and by the ability to go through the process of the acrosome reaction (release of lytic enzymes which presumably serve for penetration of the zona pellucida by the sperm) when suitably stimulated. Sperm capacitation takes place in vivo and in vitro and among other things independently of a raised bicarbonate concentration in the medium (PE Visconti & GS Kopf (1998), Biol Reprod 59:1ff; E de Lamirande et aL. 1997, Mol Hum Reprod 3(3):175ff). Sperm capacitation can also be stimulated by adding suitable membrane-passing cAMP analogs, e.g. db-cAMP, and an inhibitor that prevents their degradation (e.g. IBMX). The presumed dependence of sperm function on sAC was confirmed only recently by a genetic deletion model, a so-called knock-out mouse (G Esposito et al. 2004, PNAS 101(9):2993ff). Male mice lacking the gene for sAC exhibit spermatogenesis that proceeds normally, but are infertile. The sperm have motility defects and are not capable of fertilizing an egg. The animals did not display any other defects or abnormal findings, which contradicts other hypothesized functions of sAC (J H Zippin et al. 2003, FASEB 17:82ff)).

sAC has a unique sequence and only slight homology to other somatic adenylate cyclases. It is the only adenylate cyclase in mammalian sperm and the activity is essential for sperm motility and capacitation. Specific sAC inhibitors accordingly represent an important possibility for controlling male fertility.

The present invention therefore relates to medicinal products that contain at least one of the compounds as claimed in claims 1-3. The present invention also relates to the use of the compounds as claimed in claims 1-7.

For use of the compounds according to the invention as medicinal products they are converted to the form of a pharmaceutical preparation, which contains, in addition to the active substance, pharmaceutical, organic or inorganic inert vehicles that are suitable for enteral or parenteral application, for example water, gelatin, gum arabic, lactose, starch, magnesium stearate, talc, vegetable oils, polyalkylene glycols etc. The pharmaceutical preparations can be in solid form, for example as tablets, dragees, suppositories, or capsules, or in liquid form, for example as solutions, suspensions or emulsions. If necessary they also contain excipients, such as preservatives, stabilizers, wetting agents or emulsifiers; salts for altering osmotic pressure or buffers. These pharmaceutical preparations are also the object of the present invention.

Injection solutions or suspensions, especially aqueous solutions of the active compounds in polyhydroxyethoxylated castor oil, are particularly suitable for parenteral application. Surface-active excipients such as salts of bile acids or animal or vegetable phospholipids, as well as mixtures thereof and liposomes or their constituents, can also be used as carrier systems.

In particular, tablets, dragées or capsules with talc and/or hydrocarbon vehicles or binders, for example lactose, maize starch or potato starch, are suitable for oral application. Application can also be in liquid form, for example as juice, to which a sweetener is added if required. Clathrates are also suitable for oral application of these compounds, and the following may be mentioned as examples: the clathrates with alpha-, beta-, gamma-cyclodextrin or alternatively beta-hydroxypropyl-cyclodextrin.

The present invention also relates to enteral, parenteral and oral application.

The dosage of the active substances can vary depending on the route of administration, the patient's age and weight, the nature and severity of the disease to be treated and similar factors. The daily dose is 0.5-1000 mg, preferably 50-200 mg, and the dose can be a single dose that is to be administered once, or can be divided into 2 or more daily doses.

The compounds according to the invention of general Formula I are, among other things, excellent inhibitors of soluble adenylate cyclase. Inhibitors of soluble adenylate cyclase lead to depression of the cAMP signal. The cAMP level is decisive for control of the processes that play an important role in cell proliferation, cell differentiation and apoptosis. Diseases, e.g. cancer, in which depression of the cAMP level is decisive, can be modulated by inhibitors of soluble adenylate cyclase. This modulation can have prophylactic and therapeutic effects for patients suffering such a disease. At the present time diseases which are, like cancer, associated with increased cell proliferation, are treated for example by radiotherapy and chemotherapy. These methods are nonspecific and have a high potential for side-effects. The provision of new substances, which act directly on particular target sites, is therefore advantageous. The present invention relates to substances that modulate cAMP production by the inhibition of soluble adenylate cyclase. For example, abnormal cell proliferation can be reduced or prevented by regulation or inhibition of cAMP production. Soluble adenylate cyclase can be inhibited by the use of the substances according to the invention, with a consequent reduction in cell proliferation. The present invention relates to medicinal products for the treatment of diseases that contain at least one compound according to general Formula I, and medicinal products with suitable vehicles and excipients. The diseases are characterized in that they are caused by disturbances of metabolism of the second messenger cAMP.

Lowering of the cAMP concentration by inhibition of soluble adenylate cyclase can provide a means of modulation of sperm capacitation. The present invention relates to the use of the substances according to the invention for the lowering and/or inhibition of male gamete fertility, mediated by the reduction or inhibition of soluble adenylate cyclase activity and accordingly of sperm capacitation.

Fertilization of the ovum can be prevented by administering an effective amount of a substance that leads to inhibition of cAMP production. The present invention also relates to the use of the compound of general Formula I for the production of a medicinal product for non-hormonal contraception.

If the production of the starting compounds is not described, these are known or can be produced similarly to known compounds or methods described here. It is also possible to carry out all the reactions described here in parallel reactors or using combinatorial techniques.

The mixtures of isomers can be separated into the enantiomers or E/Z isomers by usual methods, for example crystallization, chromatography or salt formation.

The salts are produced in the usual manner, by adding the equivalent amount or an excess of a base or acid, which is in solution if necessary, to a solution of the compound of Formula I, separating the precipitate or processing the solution in the usual way.

Production of the compounds according to the invention

The following examples explain the production of the compounds of general Formula I according to the invention, without limiting the scope of the claimed compounds to these examples.

The compounds of general Formula I according to the invention can be produced as described below.

Step 1: Amide coupling:

Dissolve a carboxylic acid (1.0 equivalent) in N,N-dimethylformamide (DMF) (10 ml/1 mmol), and add N-[(dimethylamino)-1H-1,2,3-triazolo[4,5-b]-pyridin-1-ylmethylene]-N-methylmethanaminiumhexafluorophosphate-N-oxide (HATU) (1.1 equivalent) and the amine for coupling (1.0 equivalent). Then add ethyldiisopropylamine (1.1 equivalent) at 0° C. and stir the mixture for 22 hours at room temperature. Then add ice water to the mixture (35 ml/1 mmol carboxylic acid), and stir for 30 min at room temperature. Filter the precipitated crystals with suction and dry in air. Use the product in the next stage either without further purification or purified chromatographically. If no crystals form, after removing the DMF extract the aqueous phase with ethyl acetate or dichloromethane, combine the organic phases and dry over sodium sulfate. After removing the solvent, carry out chromatographic purification of the residue.

Step 2: Reduction of the nitro group:

Place the nitro compound (1.0 equivalent) in methanol (10 ml/1 mmol) and water (0.03 ml/1 mmol), add ammonium formate (5 equivalent) and catalytic amounts of palladium on carbon (10%) and heat for 3 hours at ]0° C. under reflux. Then filter through Celite with suction and rinse with boiling methanol. After removing the solvent, add water to the residue (7 ml/1 mmol amide) and filter off the precipitated crystals with suction. If no crystals form, extract the aqueous phase with ethyl acetate or dichloromethane. Wash the combined organic phases with saturated sodium chloride solution and dry over sodium sulfate. Then remove the solvent under reduced pressure.

Step 3: Coupling with arylsulfonyl chlorides

Dissolve the resulting amine (1.0 equivalent) in DMF (10 ml/1 mmol), add, at 0° C. ethyldiisopropylamine (1.5 equivalent) and arylsulfonyl chloride (1.0 equivalent) and stir for one hour at room temperature. Remove the solvent under reduced pressure and purify the residue chromatographically.

Step 4: Bromination

Dissolve the compound to be brominated (1.0 equivalent) in tetrahydrofuran (5 ml/1 mmol) and add N-bromosuccinimide (1.0 equivalent). After 30 min add water, and 20 min later filter off the precipitated crystals with suction. If no crystals form, extract the aqueous phase with ethyl acetate and dry the combined organic phases over sodium sulfate. After removing the solvent, carry out chromatographic purification of the residue.

Step 5: Saponification

Add 19 equivalent of a 1M sodium hydroxide solution in ethanol/water (1/1) to the ester compounds (1.0 equivalent). After 6 hours at room temperature, remove the ethanol under reduced pressure, dilute with water and adjust to pH 2 with 10% aqueous sulfuric acid. Then filter off the precipitated crystals with suction.

Step 6: Coupling with arylboronic acids

Suspend the bromine compound obtained after Step 4 (1.0 equivalent) with an arylboronic acid (1.5 equivalent) in toluene/ethanol 1:1 (40 ml/1 mmol ester) and add 1M sodium carbonate solution (2.5 equivalent) and lithium chloride (2.8 equivalent). After adding tetrakis(triphenylphosphine)-palladium (0.08 equivalent), reflux the reaction mixture for 8 hours. After cooling to room temperature, dilute with ethyl acetate (70 ml/1 mmol ester) and, 10 min later, filter through Celite with suction. Wash the filtrate with saturated sodium hydrogen carbonate/saturated sodium chloride solution and dry over sodium sulfate. After removing the solvent, carry out chromatographic purification of the residue.

EXAMPLE 1

(+/−)-5-(4-tert-Butylbenzenesulfonylamino)-3-phenyl-1-benzothiophene-2-carboxylic acid-(2-hydroxypropyl)amide

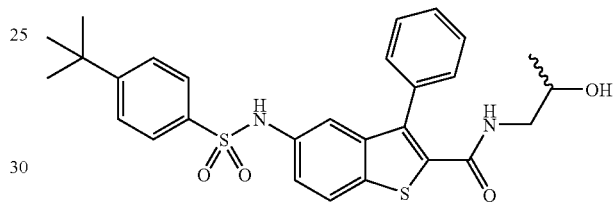

According to Step 1 after reaction of 5-(4-tert-Butylbenzenesulfonylamino)-3-phenyl-1-benzothiophene-2-carboxylic acid (155 mg, 0.33 mmol) with 1-amino-2-propanol (0.027 mL, 0.35 mmol) and subsequent chromatographic purification (silica gel, dichloromethane/methanol (0-10% methanol)), the desired compound is obtained at 17% yield (2 mg).

NMR (300 MHz, DMSO-d6): δ 0.93 (d, 3H), 1.25 (s, 9H), 3.00-3.13 (m, 2H), 3.62-3.70 (m, 1H), 4.65 (d, 1H), 6.90 (d, 2H), 7.24-7.38 (m, 6H), 7.43 (d, 2H), 7.50 (s, 1H), 7.91 (d, 1H), 8.70 (t, 1H), 9.30 (s, 1H).

The starting material for the title compound above is prepared as follows:

1 a) 5-amino-1-benzothiophene-2-carboxylic acid ethyl ester

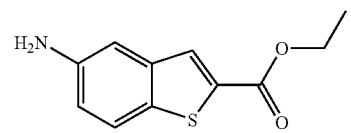

According to Step 2, after reaction of 5-nitro-1-benzothiophene-2-carboxylic acid-ethyl ester (5.0 g, 19.9 mmol) with ammonium formate (6.28 g, 99.5 mmol) in the presence of palladium on carbon (500 mg), the desired compound is obtained at 89% yield (3.92 g).

NMR (300 MHz, DMSO-d6): δ 1.25 (t, 3H), 4.30 (q, 2H), 5.25 (s, 2H), 6.85 (dd, 1H), 7.00 (d, 1H), 7.60 (d, 1H), 7.90 (s, 1H).

1 b) 5-(4-tert-Butylbenzenesulfonylamino)-1-benzothiophene-2-carboxylic acid ethyl ester

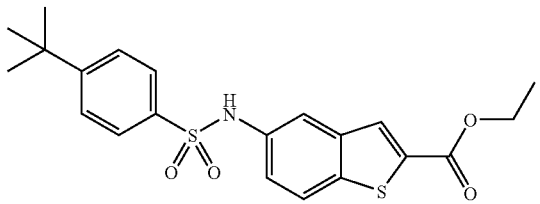

According to Step 3, after reaction of 5-amino-1-benzothiophene-2-carboxylic acid ethyl ester (3.92 g, 17.72 mmol) from Example 1a) with 4-tert-Butylbenzenesulfonyl chloride (4.12 g, 17.72 mmol) and diisopropylethylamine (6.9 mL, 26.9 mmol) followed by chromatographic purification (silica gel, hexane/ethyl acetate (0-100% ethyl acetate)), the desired compound is obtained at 72% yield (5.34 g).

NMR (300 MHz, DMSO-d6): δ 1.20 (s, 9H), 1.25 (t, 3H), 4.30 (q, 2H), 7.25 (dd, 1H), 7.52 (d, 2H), 7.68 (d, 2H), 7.72 (d, 1H), 7.88 (d, 1H), 8.10 (s, 1H), 10.45 (s, 1H).

1c) 3-Bromo-5-(4-tert-butylbenzenesulfonylamino)-1-benzothiophene-2-carboxylic acid ethyl ester

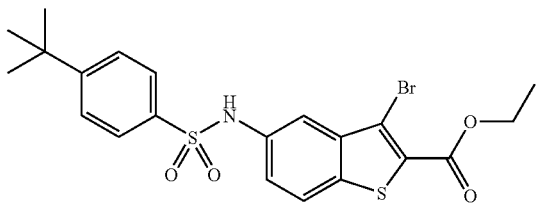

According to Step 4, after reaction of 5-(4-tert-Butylbenzenesulfonylamino)-1-benzothiophene-2-carboxylic acid ethyl ester (5.34 mg, 12.79 mmol) from Example 1b) with N-bromosuccinimide (2.30 g, 12.7 mmol) followed by chromatographic purification (silica gel, hexane/ethyl acetate (0-70% ethyl acetate)), the desired compound is obtained at 94% yield (5.98 g).

NMR (600 MHz, DMSO-d6): δ 1.25 (s, 9H), 1.32 (t, 3H), 4.35 (q, 2H), 7.30 (d, 1H), 7.55 (d, 2H), 7.64 (d, 2H), 7.92 (s, 1H), 8.05 (d, 1H), 10.10 (s, 1H).

1d) 5-(4-tert-Butylbenzenesulfonylamino)-3-phenyl-1-benzothiophene-2-carboxylic acid-ethyl ester

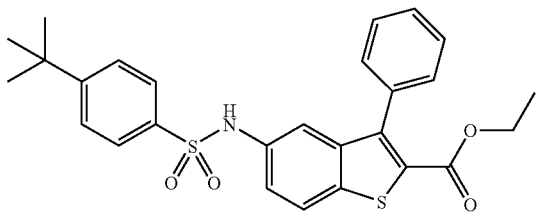

According to Step 6, after reaction of 3-Bromo-5-(4-tert-butylbenzene-sulfonylamino)-1-benzothiophene-2-carboxylic acid ethyl ester (469 mg, 1.0 mmol) from Example 1c) with phenylboronic acid (176 mg, 1.44 mmol) followed by chromatographic purification (silica gel, hexane/ethyl acetate (0-100% ethyl acetate) and ethyl acetate/methanol (0-15%)), the desired compound is obtained at 61% yield (300 mg).

NMR (300 MHz, DMSO-d6): δ 1.22 (t, 3H), 1.30 (s, 9H), 4.33 (q, 2H), 6.90 (d, 2H), 7.30-7.32 (m, 3H), 7.35-7.40 (m, 4H), 7.43 (d, 2H), 8.02 (d, 1H), 9.45 (s, 1H).

1e) 5-(4-tert-Butylbenzenesulfonylamino)-3-phenyl-1-benzothiophene-2-carboxylic acid

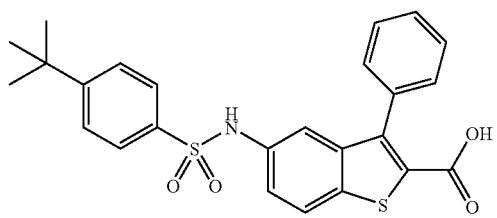

According to Step 5, after reaction of 5-(4-tert-Butylbenzenesulfonylamino)-3-phenyl-1-benzothiophene-2-carboxylic acid ethyl ester (1.24 g, 2.5 mmol) from Example 1d) with 1M sodium hydroxide solution in ethanol/water (2:1, 49 mL), the desired compound is obtained at quantitative yield (1.18 g).

NMR (300 MHz, DMSO-d6): δ 1.30 (s, 9H), 6.92 (d, 2H), 7.30-7.42 (m, 7H), 7.50 (d, 2H), 8.03 (d, 1H), 9.45 (s,1 H).

EXAMPLE 2

(+/−)-5-(4-tert-Butylbenzenesulfonylamino)-3-phenyl-1-benzothiophene-2-carboxylic acid-(2-hydroxy-1-methylethyl)amide

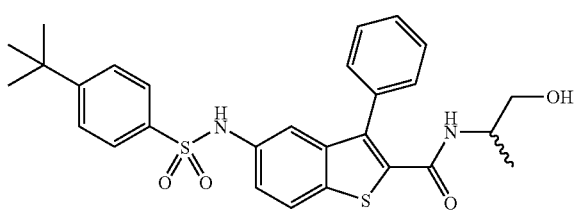

According to Step 1, after reaction of 5-(4-tert-Butylbenzenesulfonylamino)-3-phenyl-1-benzothiophene-2-carboxylic acid (155 mg, 0.33 mmol) with 2-amino-1-propanol (0.027 mL, 0.35 mmol) followed by chromatographic purification (silica gel, dichloromethane/methanol (0-10% methanol)) and recrystallization from ethyl acetate/hexane, the desired compound is obtained at 29% yield (51 mg).

NMR (300 MHz, DMSO-d6): δ 1.03 (d, 3H), 1.25 (s, 9H), 3.15-3.40 (m, 2H), 3.82-3.92 (m, 1H); 4.65 (t, 1H), 6.92 (d, 2H), 7.25-7.38 (m, 6H), 7.42 (d, 2H), 7.50 (s, 1H), 7.92 (d, 1H), 8.40 (d, 1H), 9.25 (s, 1H).

EXAMPLE 3

5-(4-tert-Butylbenzenesulfonylamino)-3-phenyl-1-benzothiophene-2-carboxylic acid-(tetrahydropyran-4-yl)amide

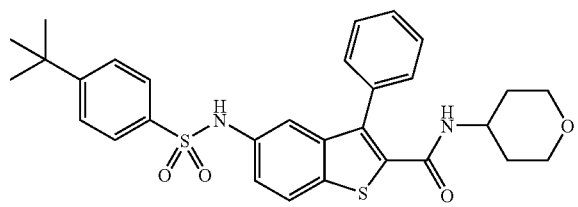

According to Step 1, after reaction of 5-(4-tert-Butylbenzenesulfonylamino)-3-phenyl-1-benzothiophene-2-carboxylic acid (155 mg, 0.33 mmol) with 4-aminotetrahydropyrane (22 mg, 0.35 mmol), the desired compound is obtained at 50% yield (92 mg).

NMR (300 MHz, DMSO-d6): δ 1.25 (s, 9H), 1.40-1.52 (m, 2H), 1.62-1.70 (m, 2H), 3.20-3.40 (m, 2H and water), 3.75-3.82 (m, 2H), 3.84-3.93 (m, 1H), 6.92 (d, 2H), 7.26-7.38 (m, 6H), 7.43 (d, 2H), 7.48 (s, 1H), 7.92 (d, 1H), 8.55 (d, 1H), 9.25 (s, 1H).

EXAMPLE 4

5-(4-tert-Butylbenzenesulfonylamino)-3-phenyl-1-benzothiophene-2-carboxylic acid-(2-morpholin-4-ylethyl)amide

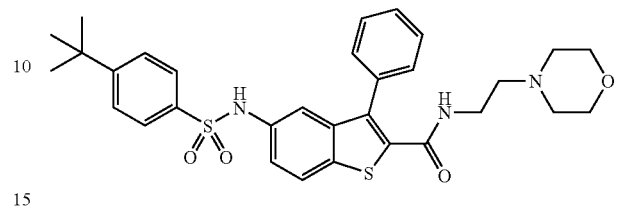

According to Step 1, after reaction of 5-(4-tert-Butylbenzenesulfonylamino)-3-phenyl-1-benzothiophene-2-carboxylic acid (155 mg, 0.33 mmol) with N—(2-aminoethyl)-morpholine (0.046 mL, 0.35 mmol) followed by chromatographic purification (silica gel, dichloromethane/methanol (0-10% methanol)) and recrystallization from ethyl acetate/hexane, the desired compound is obtained at 14% yield (27 mg).

NMR (300 MHz, DMSO-d6): δ 1.26 (s, 9H), 2.25-2.38 (m, 6H), 3.20-3.30 (m, 2H), 3.45-3.52 (m, 4H), 6.92 (d, 2H), 7.22-7.40 (m, 6H), 7.42-7.48 (m, 3H), 7.92 (d, 1H), 8.65 (t, 1H), 9.32 (s, 1H).

The following compounds were produced by analogy:

| # | Designation | Structure |
|---|---|---|
| 5 | 5-(4-tert-Butylbenzenesulfonylamino)-3-phenyl-1-benzofuran-2-carboxylic acid-(tetrahydropyran-4-yl)amide | 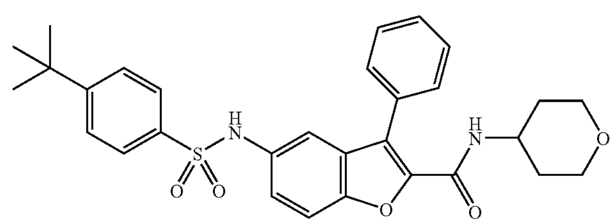 |
| 6 | 5-(4-tert-Butylbenzenesulfonylamino)-3-phenyl-1-benzofuran-2-carboxylic acid-(2-morpholin-4-ylethyl)amide | 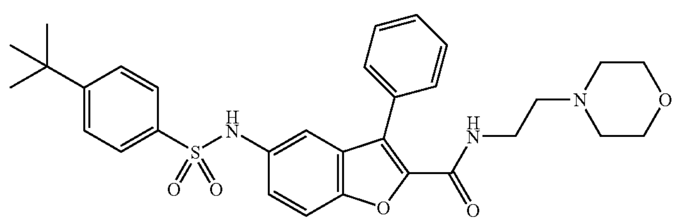 |
| 7 | 5-(4-tert-Butyl-phenylsulfonylamino)-3-phenyl-benzo[b]thiophene-2-carboxylic acid-(3-morpholin-4-yl-propyl)-amide | 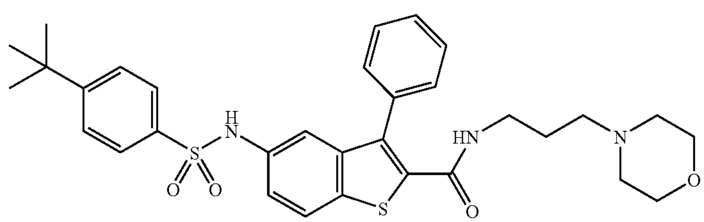 |

-continued

| # | Designation | Structure |
|---|---|---|
| 8 | 5-(4-tert-Butyl-phenylsulfonylamino)-3-phenyl-benzo[b]thiophene-2-carboxylic acid-cyclopentyl-amide | 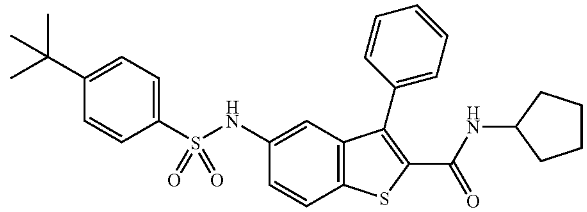 |
| 9 | 5-(4-tert-Butyl-phenylsulfonylamino)-3-phenyl-benzo[b]thiophene-2-carboxylic acid-(4-pyridyl)-amide | 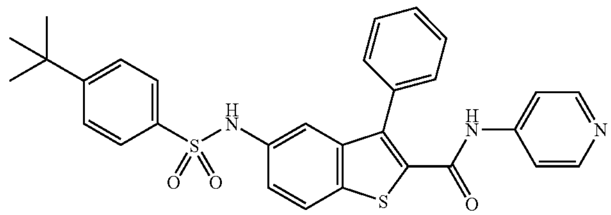 |
| 10 | 5-(4-tert-Butyl-phenylsulfonylamino)-3-phenyl-benzo[b]thiophene-2-carboxylic acid-(2-methoxy-ethyl)-amide | 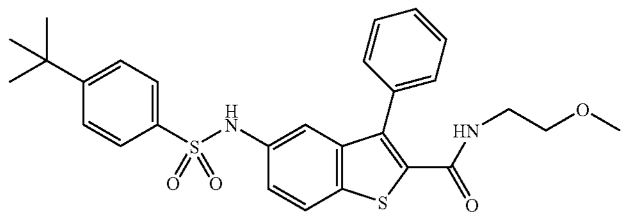 |
| 11 | 5-(4-tert-Butyl-phenylsulfonylamino)-3-phenyl-benzo[b]thiophene-2-carboxylic acid-cyclohexyl-amide | 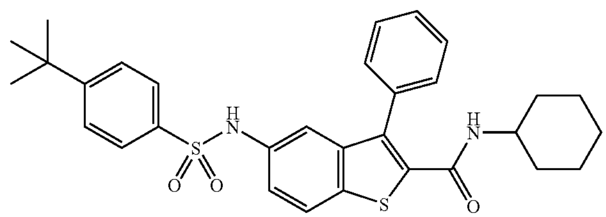 |
| 12 | 5-(4-tert-Butyl-phenylsulfonylamino)-3-phenyl-benzo[b]thiophene-2-carboxylic acid-(2-hydroxy-ethyl)-amide | 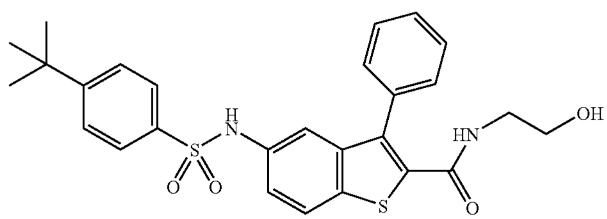 |
| 13 | 5-(4-tert-Butyl-phenylsulfonylamino)-3-phenyl-benzo[b]thiophene-2-carboxylic acid-(2-propen-1-yl)-amide | 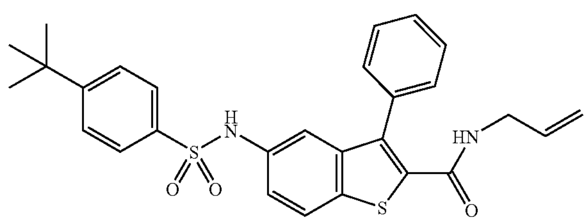 |
| 14 | 5-(4-tert-Butyl-phenylsulfonylamino)-3-phenyl-benzo[b]thiophene-2-carboxylic acid-(2-acetylamino-ethyl)-amide | 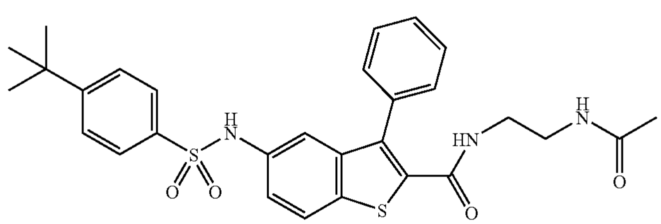 |

-continued

| # | Designation | Structure |
|---|---|---|
| 15 | 5-(4-tert-Butyl-phenylsulfonylamino)-3-phenyl-benzo[b]thiophene-2-carboxylic acid-(5-hydroxy-4,4-dimethyl-pentyl)-amide | 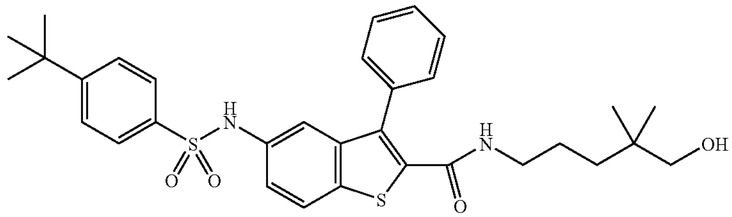 |
| 16 | (+/−)-5-(4-tert-Butylphenylsulfonylamino)-3-phenyl-1-benzofuran-2-carboxylic acid-(2-hydroxypropyl)amide | 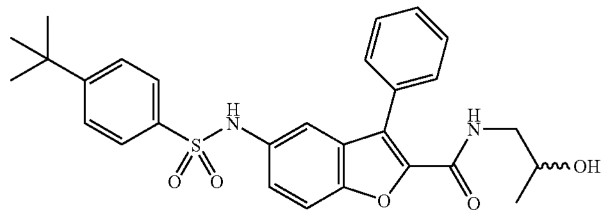 |
| 17 | (+/−)-5-(4-tert-Butylbenzenesulfonylamino)-3-phenyl-1-benzofuran-2-carboxylic acid-(2-hydroxy-1-methylethyl)amide | 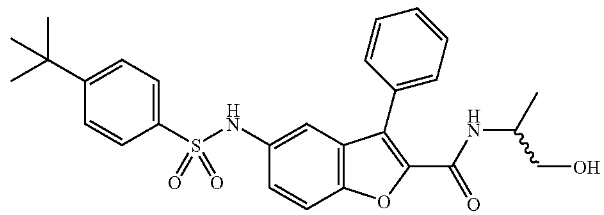 |

Biological examples

EXAMPLE 1 sAC assay

In a suitable buffer system, soluble, sperm-specific adenylate cyclase catalyzes the conversion of adenosine triphosphate (ATP) to cyclic adenosine monophosphate (cAMP) and pyrophosphate. Free cAMP generated in this way is then used in a competitive detection technique, in which the binding of a europium cryptate Eu[K]-labeled anti-cAMP antibody (anti-cAMP-Eu[K]-AB) to a modified allophycocyanine-1 molecule labeled with cAMP molecules (cAMP-XL665) is prevented. In the absence of exogenous cAMP, after excitation at 335 nm there is Fluorescence Resonance Energy Transfer (FRET) between the anti-cAMP-Eu[K]-AB (FRET donor) and the cAMP-XL665 molecule (FRET acceptor). This process is quantified, time-resolved, on the basis of the emission of the FRET acceptor XL665 (665 nm and 620 nm). A decrease in signal (measured as Well Ratio; calculated from the Formula: [(E665 nm/E620 nm)×10000]) can be attributed to the presence of cAMP and thus to the activity of sAC. First, 1.5 µl of the test substance (in 30% DMSO) is placed in each well of a 384-well test plate (polystyrene; 384, NV), and in the solvent controls only 30% DMSO. Then 10 µl of a dilute sAC enzyme solution is applied (enzyme stock solution in 300 mM NaCl, 10% glycerol; pH 7.6; enzyme intermediate and final dilution a) 1:10 and b) 1:2000 in each case in: 1.0 mM $MnCl_2$; 0.2% BSA; 50 mM Tris pH 7.5 in $H_2O$). The enzyme reaction is started by adding 5 µl of the ATP substrate solution (200 µM ATP in $H_2O$) and after incubation (25 min at room temperature) stopped by adding 5 µl of the stop solution (200 µM EDTA in PBS). Finally the whole reaction is adjusted to a total volume of 91.5 µl by adding 70 µl PBS.

Next, 8 µl of detection solution 1 is placed in a well of the 384-well measuring plate (measuring plate: polystyrene; 384, SV—black; detection solution 1: 50 µl cAMP-XL665; 950 µl reconstituted buffer; 2200 µl PBS; cAMP-XL665: prepared by adding 5 ml $H_2O$ to the lyophilized product according to the instructions in Cis bio Kit: 62AMPPEC; storage: in aliquots at −80° C.). Next, 3 µl from the 1.5 µl is added to the corresponding well of the test plate. Finally, 8 µl of detection solution 2 is added (detection solution 2: 50 µl anti-cAMP-Eu[K]-AB; 50 µl reconstituted buffer; 2200 µl PBS; anti-cAMP-Eu[K]-AB: prepared according to the instructions in Cis bio Kit: #62AMPPEC; storage: in aliquots at −80° C.). After further incubation for 90 min at room temperature, the HTRF result is measured either on the Packard Discovery or with the RubiStar HTRF measuring instrument (delay: 50 µs; integration time: 400 µs).

EXAMPLE 2

Isolation of human sperm from ejaculates and capacitation 2.1. Isolation of the sperm Human sperm from ejaculate are purified in a two-layer gradient system based on colloidal silica particles (trade name: Percoll or ISolate). Per ejaculate, 2.5 ml of pre-warmed lower layer ("90% ISolate lower layer", from Irvine) is placed in a 15 ml centrifuge tube (conical, plastic) and is carefully covered with 2.5 ml of pre-warmed upper layer ("50% ISolate upper layer", from Irvine) and held at 37° C. for <1 h on a water bath. The gradient is carefully covered with max. 3 ml of normal (with respect to sperm count, motility and liquefaction) ejaculate. Sedimentation of the sperm is carried out at 1000 × g for 25 min at room temperature. Using a glass capilllary, the two layers are removed by suction to just above the sperm pellet. For elutriation of the ISolate gradients, the sperm pellets, each resuspended in approx. 200 µl, are transferred to a 15 ml plastic tube with 12 ml mHTF medium (4 mM $NaHCO_3$; 0.01% BSA; 37° C.) and the sperm are sedimented at 1000 × g for 20 min. The medium is removed by suction to just above the pellet and adjusted with mHTF medium (4 mM $NaHCO_3$; 0.01% BSA; 37° C.) to 1000 µl. The sperm count is determined in a Neubauer counter and for subsequent capacitation is adjusted if necessary to $4\times10^6$ sperm/150 µl with mHTF medium (4 mM $NaHCO_3$; 0.01% BSA; 37° C.).

2.2. Capacitation

If the influence of test substances on the acrosome reaction is to be tested, the sperm must be preincubated with the test substances. This preincubation (15 min in a heating cabinet at 37° C.) is necessary to permit penetration of the test substances into the sperm before the start of capacitation, i.e. to achieve presaturation of the binding sites in the sperm, especially in the case of substances that do not pass through the membrane easily. It is also necessary because the increase in BSA concentration during capacitation due to the high lipid binding of the BSA could lead to a decrease in the effective concentration of test substance in the sample.

The test substances are dissolved in DMSO and diluted with mHTF medium (4 mM $NaHCO_3$; 0.01% BSA; 37° C.), so that in the final 400-µl capacitation sample the DMSO concentration is 0.5%. In each case 150 µl of sperm suspension is added by pipette to 150 µl of the aforementioned temperature-controlled solution of test substance, followed by preincubation at 37° C. for 15 min. Capacitation of the sperm is started by adding 100 µl of mHTF medium (88 mM $NaHCO_3$; 4% BSA; 37° C.). In the final 400-µl capacitation sample, the concentration of sperm is $10\times10^6$/ml, the bicarbonate concentration is 4 mM and the BSA concentration is 1%. Capacitation is carried out for 3 hours at 37° C. in the heating cabinet.

For stopping capacitation, the samples (each of 400 µl) are each transferred completely to a 15-ml sample tube with 1.5 ml mHTF (4 mM $NaHCO_3$; 37° C.), centrifuged for 5 min at 1000 × g and the supernatant is removed. This step removes both the large amount of protein and the test substances.

EXAMPLE 3

Flow cytometric determination of the acrosome reaction 3.1. Initiation of the acrosome reaction by treatment with ionophore and simultaneous CD46-FITC staining The acrosome reaction (AR) of the sperm is triggered by binding of the sperm to the zona pellucida (ZP). This releases enzymes from the acrosome, enabling the sperm to penetrate the ZP and reach the ovum. In the AR, there is partial fusion, at the sperm, of the plasma membrane with the outer acrosomal membrane (OAM). At the end the sperm head is still restricted by the inner acrosomal membrane (IAM). The CD46 antigen is only detectable at the IAM. In vitro the acrosome reaction can only be induced with a suitable concentration of the calcium ionophore A23187 on capacitated sperm, but not on uncapacitated sperm or sperm for which capacitation was inhibited by test substances. By means of the FITC-labeled anti-CD46 antibody (from Pharmingen) to the IAM, the acrosome-reacted sperm can be differentiated from the acrosome-intact sperm, in which the IAM is not exposed, in the flow cytometer. With simultaneous staining of the sperm with the DNA stain ethidium homodimer (EhD), which only stains cells that have defective DNA membranes, i.e. are dead, it is possible to distinguish dead sperm from live sperm.

Because the ionophore dilutions for initiating the AR appear to be very unstable and must be mixed with the CD46-FITC solution for simultaneous staining, the solutions cannot be prepared before the start of the test, but must be prepared during processing of the capacitation samples.

The sperm pellets are resuspended in the residue of the supernatant and are diluted with 450 µl mHTF (4 mM $NaHCO_3$; 0.01% BSA; 37° C.) on a water bath (37° C.). 100 µl aliquots of the sperm suspensions are transferred by pipette to prepared sample-FACS flow tubes (on the water bath). 150 µl of a solution with ionophore and FITC-labeled anti-CD46 antibody is added by pipette to the sperm. The final concentration is 800 nm ionophore and a 1:125 dilution of the anti-CD46 antibody in mHTF (4 mM $NaHCO_3$; 0.01% BSA; 37° C.). The sperm are incubated therein for 30 min, protected from the light, on a water bath at 37° C.

Incubation is stopped by adding 3.5 ml PBS [0.1% BSA]/sample, followed by centrifugation for 5 min at 700 × g (room temperature) and then removal of the supernatants with suction. After centrifugation, the samples are kept warm on a hot-plate until measurement.

3.2. EhD staining (for differentiation of the dead/live acrosome-reacted sperm)

500 µl of freshly prepared EhD solution (150 nm EhD in PBS [w/o BSA]; 37° C.) is added to each of the sperm pellets after removal by suction. The samples can then be measured in the flow cytometer (BD FacsCalibur). Measurement is performed at a laser excitation wavelength of 488 nm, detecting 10000 sperm per measurement. Acrosome-reacted sperm are measured via CD46-FITC in the FL-1 filter at 530 nm. Dead sperm are measured by means of EhD-DNA staining in the FL-2 filter at 634 nm. The measurement channels are correspondingly compensated relative to one another beforehand.

3.3 Evaluation

The sperm are selected as a very uniform cell population in an FSC-H (forward 10 scatter) versus SSC-H (sideward scatter) dot-blot. As two-color fluorescence staining is used, evaluation is performed by quadrant analysis in an FL-1 (EhD;

X axis) vs. FL-2 (FITC-CD46, Y axis) dot-blot with the selected sperm population from the FSC vs. SSC dot-blot:

| | Quadrant in FL-1 vs. FL-2 dot-blot | Staining | Analysis |
|---|---|---|---|
| Q1 = UL | upper left | only EhD | dead, not acrosome-reacted sperm |
| Q2 = UR | upper right | EhD and FITC-CD46 | dead, acrosome-reacted sperm |
| Q3 = LL | lower left | unstained | live, not acrosome-reacted sperm |
| Q4 = LR | lower right | only FITC-CD46 | live, acrosome-reacted sperm |

To calculate the %-induced acrosome-reacted sperm (="IAR[%]"), only the live sperm from Q3 and Q4 are taken, and their total count is set equal to 100%.

IAR is then calculated as follows:

$$IAR[\%] = \frac{LR \times 100}{LL + LR}$$

A proportion of the sperm undergo the acrosome reaction spontaneously without addition of ionophore (="SAR[%]"). Therefore a control measurement is always performed on identically-treated sperm without addition of ionophore. Calculation of SAR is similar to calculation of IAR. The acrosome reaction actually induced by the ionophore (="ARIC[%]") is calculated as the difference: ARIC =IAR-SAR.

For subsequent analysis of the influence of our inhibitors on sAC-mediated capacitation (measured as the capacity of the sperm for the ionophore-induced acrosome reaction), the percentage of acrosome-reacted sperm in the positive capacitation control (=incubation with mHTF medium with 25 mM NaHCO$_3$; 1% BSA without test substances) is set =100%. The capacity of the sperm to which the test substances have been added, for the acrosome reaction, is stated relative to this maximum acrosome reaction.

Materials used mHTF =modif. human tubular fluid (from Irvine Scientific), Dulbeccos's Phosphate-Buffered-Saline (from Gibco) (with Ca$^{2+}$, Mg$^{2+}$, 1 g/L D-glucose, 36 mg/L Na-pyruvate, w/o phenol red, w/o NaHCO$_3$); bovine serum albumin, Fraction V (from Fluka); dimethylsulfoxide (DMSO), anhydrous (from Merck); sodium bicarbonate 7.5% solution (83 mM) (from Irvine Scientific); Isolate-Gradient (from Irvine Scientific); Ionophore-A23187 free acid, (from Calbiochem); Ethidium Homodimer (EhD) (from Molecular Probe), Mouse Anti Human CD46: FITC (from Pharmingen).

References

J. W. Carver-Ward, Human Reproduction Vol. 11, No. 9, pp: 1923 ff, 1996 High fertilization prediction by flow cytometric analysis of the CD46 antigen on the inner acrosomal membrane of spermatozoa O. J. DC ruz, G. G. Haas, Fertility and Sterility Vol.65, No. 4, pp: 843 ff, 1996 Fluorescence-labeled fucolectins are superior markers for flow cytometric quantitation of the sperm acrosome reaction E. Nieschlag, H.M. Behre, Andrology, Springer Verlag 1996

EXAMPLES

| # | | R$^4$ | Y | IC$_{50}$ (μM) |
|---|---|---|---|---|
| 6 | 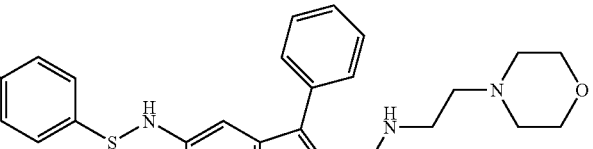 | —(CH$_2$)$_2$-morpholine | —CO | 5.2 |
| 16 | 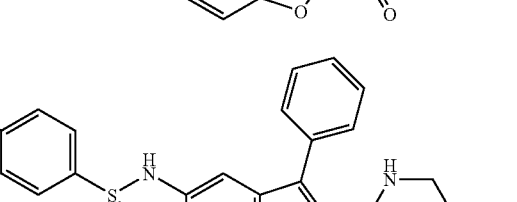 | —CH$_2$—CH(CH$_3$)—OH | —CO | 4.3 |
| 17 | 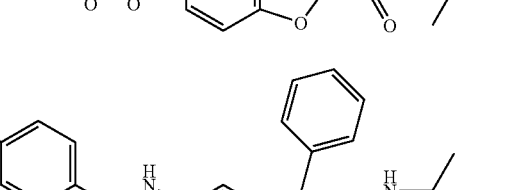 | —CHCH$_3$—CH$_2$—OH | —CO | 8.5 |

| # | R⁴ | Y | IC₅₀ (μM) |
|---|---|---|---|
| 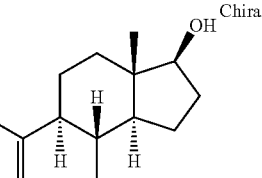 4-OH-estradiol | | | 13 |
| 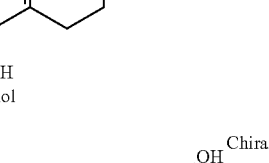 2-OH-estradiol | | | 11 |

It can be seen from the table that with respect to the inhibition of soluble adenylate cyclase, expressed by the IC$_{50}$ value, the compounds according to the invention display greater activity than the known catechol estrogens (OH-estradiols). The catechol estrogens are toxic, therefore the compounds according to the invention are superior to the known compounds.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosures of all applications, patents and publications, cited herein and of corresponding German application No. 10 2005 027 274.6, filed Jun. 8, 2005, and U.S. Provisional Application Ser. No. 60/61,776, filed Jun. 20, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of Formula 1

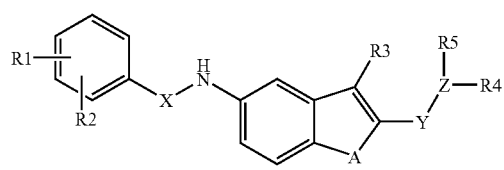

(1)

wherein
R$^1$ is hydrogen, halogen, CF$_3$, sulfonyl-C$_1$-C$_6$-alkyl, sulfonamide, cyano, C$_3$-C$_6$-cycloalkyl,
  which C$_3$-C$_6$-cycloalkyl is optionally multiply saturated and optionally multiply substituted, or
  C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl, or C$_1$-C$_6$-aryl-C$_1$-C$_6$-alkyl,
  which C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl or C$_1$-C$_6$-aryl-C$_1$-C$_6$-alkyl is optionally be interrupted singly or more than once, identically or differently by oxygen, sulfur or nitrogen,
R$^2$ is halogen, CF$_3$, sulfonyl-C$_1$-C$_6$-alkyl, sulfonamide, cyano,
  C$_3$-C$_6$-cycloalkyl,
  which C$_3$-C$_6$-cycloalkyl is optionally multiply saturated and optionally multiply substituted, or
  C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl,C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl, or C$_1$-C$_6$-aryl-C$_1$-C$_6$-alkyl, which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl or $C_1$-$C_6$-aryl-$C_1$-$C_6$-alkyl is optionally interrupted singly or more than once, identically or differently by oxygen, sulfur or nitrogen, $R^3$ is $C_6$-$C_{12}$-aryl,
 which $C_6$-$C_{12}$-aryl is optionally substituted singly or more than once, identically or differently with halogen, $C_1$-$C_6$-alkoxy, hydroxy, cyano, $CO_2$—($C_1$-$C_6$-alkyl), N—($C_1$-$C_6$-alkyl)$_2$, CO—$NR^4R^5$, $CF_3$, $C_1$-$C_6$-alkyl or $C_1$-$C_6$-acyl,
  which $C_1$-$C_6$-alkyl or $C_1$-$C_6$-acyl is optionally singly or more than once substituted,
 $C_5$-$C_{12}$-heteroaryl,
 which $C_5$-$C_{12}$-heteroaryl is optionally substituted singly or more than once, identically or differently with halogen, $C_1$-$C_6$-alkyl, $C_1$-$C_6$-acyl, $C_1$-$C_6$-alkoxy, hydroxy, cyano, $CO_2$—($C_1$-$C_6$-alkyl), N—($C_1$-$C_6$-alkyl)$_2$, CO—$NR^4R^5$ or $CF_3$, or
 $C_3$-$C_6$-cycloalkyl,
 which $C_3$-$C_6$-cycloalkyl is optionally substituted singly or more than once, identically or differently with halogen, $CF_3$ hydroxy, cyano, $CO_2$—($C_1$-$C_6$-alkyl), $C_1$-$C_6$-alkyl, $C_1$-$C_6$-acyl, N—($C_1$-$C_6$-alkyl)$_2$, CO—$NR^4R^5$ or $C_1$-$C_6$-alkoxy, $R^4$ is hydrogen,
 $C_3$-$C_6$-cycloalkyl,
  which $C_3$-$C_6$-cycloalkyl is optionally substituted singly or more than once, identically or differently with $C_1$-$C_6$-alkyl, $C_1$-$C_6$-acyl, $C_1$-$C_6$-alkoxy or $CF_3$,
 $C_6$-$C_{12}$-aryl,
  which $C_6$-$C_{12}$-aryl is optionally substituted singly or more than once, identically or differently with halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano,
 $C_5$-$C_{12}$-heteroaryl,
  which $C_5$-$C_{12}$-heteroaryl is optionally substituted singly or more than once, identically or differently with halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano, or
 $C_1$-$C_6$-alkyl,
  which $C_1$-$C_6$-alkyl is optionally substituted, $R^5$ is hydrogen,
 $C_3$-$C_6$-cycloalkyl,
  which $C_3$-$C_6$-cycloalkyl is optionally substituted singly or more than once, identically or differently with $C_1$-$C_6$-alkyl, $C_1$-$C_6$-acyl, $C_1$-$C_6$-alkoxy or $CF_3$,
 $C_6$-$C_{12}$-aryl,
  which $C_5$-$C_{12}$-heteroaryl is optionally substituted singly or more than once, identically or differently with halogen, with $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano, or
 $C_5$-$C_{12}$-heteroaryl,
  which $C_5$-$C_{12}$-heteroaryl is optionally substituted singly or more than once, identically or differently with halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano, or
 $C_1$-$C_6$-alkyl,
  which $C_1$-$C_6$-alkyl is optionally ean-be substituted,
or alternatively
$R^4$ and $R^5$ together form a 5-8-membered ring, which optionally further contains one or more heteroatoms,
X is sulfonyl, $(CH_2)_n$ or carbonyl,
Y is —$(CH_2)_n$— or carbonyl, Z is nitrogen,
A is oxygen or sulfur, and
n is 0-4,
or a diastereomer, enantiomer or salt thereof.

2. A compound of claim 1, wherein:
$R^1$ is hydrogen, halogen, $CF_3$, a $C_3$-$C_6$-cycloalkyl, sulfonyl-$C_1$-$C_6$-alkyl, sulfonamide, or cyano, $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, or $C_1$-$C_6$-aryl-$C_1$-$C_6$-alkyl,
 which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl or $C_1$-$C_6$-aryl-$C_1$-$C_6$-alkyl is optionally interrupted singly or more than once, identically or differently by oxygen, sulfur or nitrogen, $R^2$ is halogen, $CF_3$, $C_3$-$C_6$-cycloalkyl, sulfonyl-$C_1$-$C_6$-alkyl, sulfonamide, cyano, $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, or $C_1$-$C_6$-aryl-$C_1$-$C_6$-alkyl,
 which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, C 1-$C_6$-acyl-$C_1$-$C_6$-acyl, $C_1$-$C_6$-alkyl-$C_1$-$C_6$-aryl or $C_1$-$C_6$-aryl-$C_1$-$C_6$-alkyl is optionally interrupted singly or more than once, identically or differently by oxygen, sulfur or nitrogen, $R^3$ is $C_6$-$C_{12}$-aryl,
 which $C_6$-$C_{12}$-aryl is optionally substituted singly or more than once, identically or differently with halogen, $C_1$-$C_6$-alkyl, $C_1$-$C_3$-acyl, $C_1$-$C_3$-alkoxy, cyano, hydroxy, N—$(CH_3)_2$, $CO_2$—($C_1$-$C_3$-alkyl), CO—$NR^4R^5$ or $CF_3$, $C_5$-$C_{12}$-heteroaryl,
 which $C_5C_{12}$-heteroaryl is optionally substituted singly or more than once, identically or differently with chlorine fluorine, $C_1$-$C_6$-alkyl, $C_1$-$C_3$-acyl, $C_1$-$C_3$-alkoxy, cyano, hydroxy, N—$(CH_3)_2$, $CO_2$—($C_1$-$C_3$-alkyl), CO—$NR^4R^5$ or $CF_3$, or
 $C_3$-$C_6$-cycloalkyl,
 which $C_3$-$C_6$-cycloalkyl is optionally substituted singly or more than once, identically or differently with chlorine, fluorine, $CF_3$ cyano, $C_1$-$C_3$-alkyl, $C_1$-$C_3$-acyl, hydroxy, N—$(CH_3)_2$, $CO_2$—($C_1$-$C_3$-alkyl), CO—$NR^4R^5$ or $C_1$-$C_3$-alkoxy, $R^4$ is hydrogen,
 $C_3$-$C_6$-cycloalkyl,
  which $C_3$-$C_6$-cycloalkyl is optionally substituted singly or more than once, identically or differently with $C_1$-$C_3$-alkyl, $C_1$-$C_3$-acyl, $C_1$-$C_3$-alkoxy or $CF_3$,
 $C_6$-$C_{12}$-aryl,
  which $C_6$-$C_{12}$-aryl is optionally substituted singly or more than once, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or
 $C_1$-$C_6$-alkyl,
  which $C_1$-$C_6$-alkyl is optionally substituted, $R^5$ is hydrogen,
 $C_3$-$C_6$-cycloalkyl,
  which $C_3$-$C_6$-cycloalkyl is optionally substituted singly or more than once, identically or differently with $C_1$-$C_3$-alkyl, $C_1$-$C_3$-acyl, $C_1$-$C_3$-alkoxy or $CF_3$,
 $C_6$-$C_{12}$-aryl,
  which $C_6$-$C_{12}$-aryl is optionally substituted singly or more than once, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, $C_5$-$C_{12}$-heteroaryl,
which $C_5$-$C_{12}$-heteroaryl is optionally substituted singly or more than once, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or $C_1$-$C_6$-alkyl,
which $C_1$-$C_6$-alkyl is optionally substituted, or alternatively $R^4$ and $R^5$ together form a 5-8-membered ring, which optionally further contains one or more heteroatoms, X is sulfonyl, $(CH_2)_n$ or carbonyl, Y is —$(CH_2)$—°or carbonyl, Z is nitrogen, A is oxygen or sulfur, and n stands for 0-2, or a diastereomer, enantiomer or salt thereof.

3. A compound of claim 1, wherein:

$R^1$ is hydrogen, $R^2$ is $C_3$-$C_6$-cycloalkyl, $C_1$-$C_6$-alkyl, $CF_3$, cyano, bromine, —$OCF_3$, —$SO_2$—$CH_3$, $R^3$ is $C_6$-$C_{12}$-aryl,
which $C_6$-$C_{12}$-aryl is optionally substituted singly or more than once, identically or differently with halogen, $C_1$-$C_6$-alkyl, $C_1$-$C_3$-acyl, $C_1$-$C_3$-alkoxy, cyano, hydroxy, N—$(CH_3)_2$, $CO_2$—$(C_1$-$C_3$-alkyl), CO—$NR^4R^5$ or $CF_3$, $C_5$-$C_{12}$-heteroaryl,
which $C_5$-$C_{12}$-heteroaryl is optionally substituted singly or more than once, identically or differently with chlorine, fluorine, $C_1$-$C_6$-alkyl, $C_1$-$C_3$-acyl, $C_1$-$C_3$-alkoxy, cyano, hydroxy, N—$(CH_3)_2$, $CO_2$—$(C_1$-$C_3$-alkyl), CO—$NR^4R^5$ or $CF_3$, $C_3$-$C_6$-cycloalkyl,
which $C_3$-$C_6$-cycloalkyl is optionally substituted singly or more than once, identically or differently with chlorine, fluorine, $CF_3$ cyano, $C_1$-$C_3$-alkyl, $C_1$-$C_3$-acyl, hydroxy, N—$(CH_3)_2$, $CO_2$—$(C_1$-$C_3$-alkyl), CO—$NR^4R^5$ or $C_1$-$C_3$-alkoxy, $R^4$ is hydrogen, $C_3$-$C_6$-cycloalkyl,
which $C_3$-$C_6$-cycloalkyl is optionally substituted singly or more than once, identically or differently with $C_1$-$C_3$-alkyl, $C_1$-$C_3$-acyl, $C_1$-$C_3$-alkoxy or $CF_3$, $C_6$-$C_{12}$-aryl,
which $C_6$-$C_{12}$-aryl is optionally substituted singly or more than once, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, $C_5$-$C_{12}$-heteroaryl,
which $C_5$-$C_{12}$-heteroaryl is optionally substituted singly or more than once, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or $C_1$-$C_6$-alkyl,
which $C_1$-$C_6$-alkyl is optionally substituted, $R^5$ is hydrogen, X is sulfonyl, carbonyl or —$(CH_2)_n$, Y is —$(CH_2)_n$— or carbonyl, Z is nitrogen, A is oxygen or sulfur, and n is 0-2, or a diastereomer, enantiomer or salt thereof.

4. A compound of claim 1, wherein:

$R^1$ is hydrogen, $R^2$ is $C_3$-$C_6$-cycloalkyl, $C_1$-$C_6$-alkyl, $CF_3$, cyano, bromine, or —$OCF_3$, —$SO_2$—$CH_3$ in the para-position, $R^3$ is $C_6$-$C_{12}$-aryl,
which $C_6$-$C_{12}$-aryl is optionally substituted singly or twice, identically or differently with halogen, $C_1$-$C_3$-alkyl, acetyl, methoxy, ethoxy, cyano, hydroxy, N—$(CH_3)_2$, $CO_2$—$(C_1$-$C_3$-alkyl), CO—$NHR^5$ or $CF_3$, $C_5$-$C_{12}$-heteroaryl,
which $C_5$-$C_{12}$-heteroaryl is optionally substituted singly or twice, identically or differently with chlorine, fluorine, $C_1$-$C_3$-alkyl, acetyl, methoxy, ethoxy, cyano, hydroxy, N—$(CH_3)_2$, $CO_2$—$(C_1$-$C_3$-alkyl), CO—$NHR^5$ or $CF_3$, $C_3$-$C_6$-cycloalkyl, is hydrogen, $C_3$-$C_6$-cycloalkyl, Which $C_3$-$C_6$-cycloalkyl is optionally substituted singly or more than once, identically or differently with $C_1$-$C_3$-alkyl, $C_1$-$C_3$-acyl, $C_1$-$C_3$-alkoxy or $CF_3$, $C_6$-$C_{12}$-aryl,
which $C_6$-$C_{12}$-aryl is optionally substituted singly or more than once, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, $C_5$-$C_{12}$-heteroaryl,
which $C_5$-$C_{12}$-heteroaryl is optionally substituted singly or more than once, identically or differently with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano, or $C_1$-$C_6$-alkyl,
which $C_1$-$C_6$-alkyl is optionally substituted $R^5$ is hydrogen, X is sulfonyh carbonyl or —$(CH_2)_n$, Y is —$(CH_2)_n$— or carbonyl, Z is nitrogen, A is oxygen or sulfur and n is 1–2 or a diastereomer, enantiomer or salt thereof.

5. A compound of claim 1, wherein:

$R^1$ is hydrogen, $R^2$ is tertiary butyl, iso-propyl, iso-butyl, sec. butyl, cyano, bromine, or —O—$CF_3$, —$SO_2$-$CH_3$ in the para-position, $R^3$ is one of the following groups

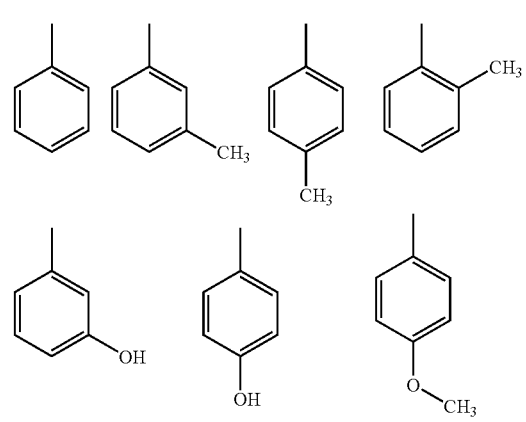

-continued

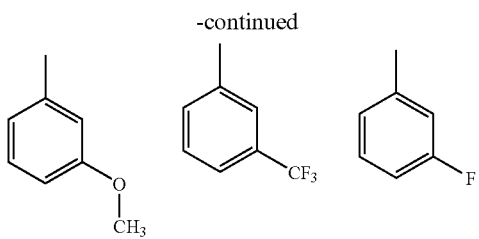

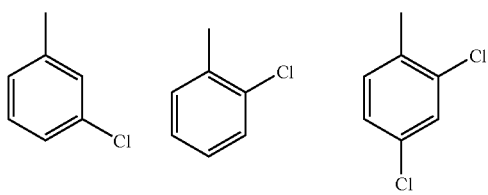

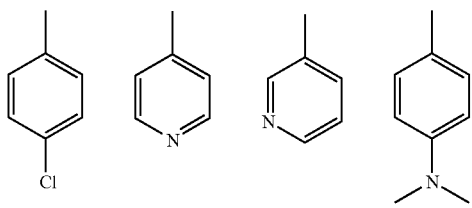

R⁴ is hydrogen or —(CH₂)ₙ—N—(CH₃)₂, —(CH2)₂—CH₃, —(CH₂)₂—NH—COCH₃, —(CH₂)—CHCH₃—OH, —(CH2)₂—O—CH₃, —(CH2)₂—OH, —CHCH₃—CH₂—OH, —(CH₂)₃—CH(CH₃)₂—CH₂—OH or CH₂—CN, or one of the following groups

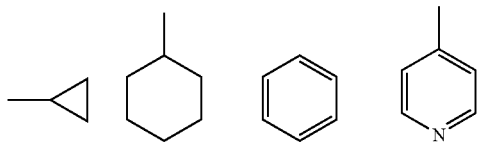

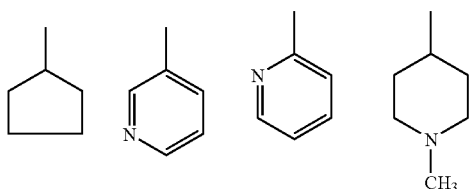

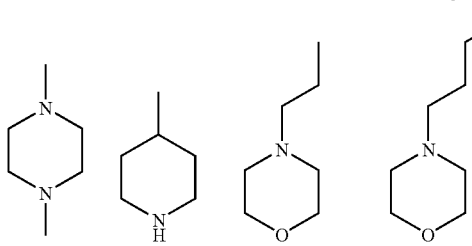

-continued

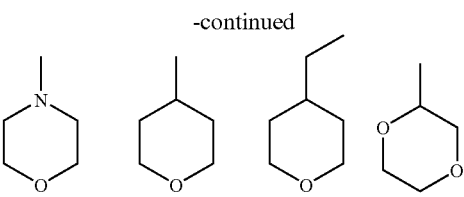

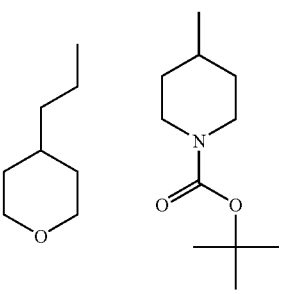

R⁵ is hydrogen,
X is sulfonyh carbonyl or —(CH₂)ₙ,
Y is —(CH₂)ₙ— or carbonyl,
Z is nitrogen,
A is oxygen or sulfur, and
n is 1–2
or a diastereomer, enantiomer or salt thereof.

6. A compound of claim 1, wherein:
R¹ is hydrogen,
R² is tertiary butyl, iso-propyl, iso-butyl, sec. butyl, cyano, bromine, or —O—CF₃, or —SO₂—CH₃ in the para-position,
R³ is one of the following groups

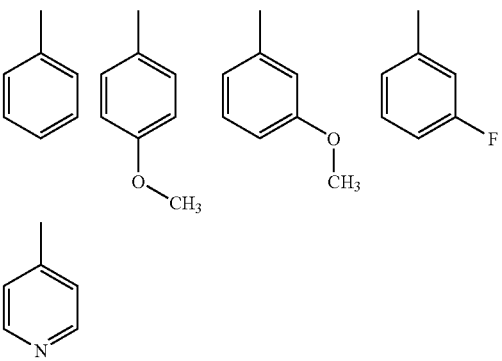

R⁴ is hydrogen or the group, —(CH₂)—CHCH₃—OH, —(CH₂)₂—O—CH₃, —CHCH₃—CH2—OH, , (CH₂)₃—CH(CH₃)₂—CH₂—OH or CH₂—CN, or one of the following groups

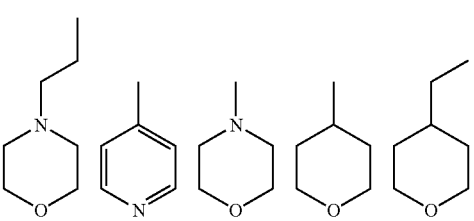

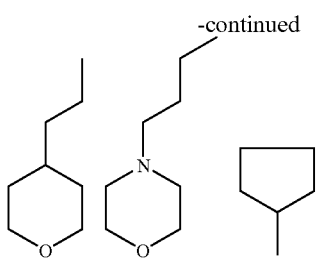

R⁵ is hydrogen,
X is sulfony, carbonyl or —(CH₂)ₙ,
Y is —(CH₂)ₙ— or carbony,
Z is nitrogen,
A is oxygen or sulfur, and
n is 1–2.
or a diastereomer, enantiomer or salt thereof.

7. A compound of claim 1, which:
(+/−)-5-(4-tert-Butylbenzenesulfonylamino)-3-phenyl-1-benzothiophene-2-carboxylic acid-(2-hydroxypropyl) amide
(+/−)-5-(4-tert-Butylbenzenesulfonylamino)-3-phenyl-1-benzothiophene-2-carboxylic acid-(2-hydroxymethyl-ethyl)amide
5-(4-tert-Butylbenzenesulfonylamino)-3-phenyl-1-benzothiophene-2-carboxylic acid -(tetrahydropyran-4-yl) amide
5-(4-tert-Butylbenzenesulfonylamino)-3-phenyl-1-benzothiophene-2-carboxylic acid-(2-morpholin-4-yl-ethyl)amide
5-(4-tert-Butylbenzenesulfonylamino)-3-phenyl-1-benzofuran-2-carboxylic acid -(tetrahydropyran-4-yl) amide
5-(4-tert-Butylbenzenesulfonylamino)-3-phenyl-1-benzofuran-2-carboxylic acid-(2-morpholin-4-yl-ethyl) amide
5-(4-tert-Butyl-phenylsulfonylamino)-3-phenyl-benzo[b]thiophene-2-carboxylic acid-(3-morpholin-4-yl-propyl)-amide
5-(4-tert-Butyl-phenylsulfonylamino)-3-phenyl-benzo[b]thiophene-2-carboxylic acid -cyclopentyl-amide
5-(4-tert-Butyl-phenylsulfonylamino)-3-phenyl-benzo[b]thiophene-2-carboxylic acid-(4-pyridyl)-amide
5-(4-tert-Butyl-phenylsulfonylamino)-3-phenyl-benzo[b]thiophene-2-carboxylic acid-(2-methoxy-ethyl)-amide
5-(4-tert-Butyl-phenylsulfonylamino)-3-phenyl-benzo[b]thiophene-2-carboxylic acid -cyclohexyl-amide -
5-(4-tert-Butyl-phenylsulfonylamino)-3-phenyl-benzo[b]thiophene-2-carboxylic acid-(2-hyxdroxy-ethyl)-amide
5-(4-tert-Butyl-phenylsulfonylamino)-3-phenyl-benzo[b]thiophene-2-carboxylic acid-(2-propen-1-yl)-amide
5-(4-tert-Butyl-phenylsulfonylamino)-3-phenyl-benzo[b]thiophene-2-carboxylic acid-(2-acetylamino-ethyl)-amide
5-(4-tert-Butyl-phenylsulfonylamino)-3-phenyl-benzo[b]thiophene-2-carboxylic acid-(5-hydroxy-4,4-dimethyl-pentyl)-amide
(+/−)-5-(4-tert-Butylphenylsulfonylamino)-3-phenyl-1-benzofuran-2-carboxylic acid-(2-hydroxypropyl)amide or
(+/−)-5-(4-tert-Butylbenzenesulfonylamino)-3-phenyl-1-benzofuran-2-carboxylic acid-(2-hydroxy-1-methyl-ethyl)amide.

8. A method for contraception. comphsing administering an effective amount of a compound of claim 1 to a subject in need thereof.

9. A method for the inhibition of soluble adenylate cyclase. comprising administering an effective amount of a compound of claim 1 to a subject in need thereof.

10. A pharmaceutical composition, compnsing a compound of claim 1 and a pharmaceutically acceptable carrier.

11. A pharmaceutical composition according to claim 10, which is suitable for enteral, parenteral or oral administration.

12. A method for contraception, comprising administering an effective amount of a compound of claim 7 to a subject in need thereof.

13. A method for the inhibition of soluble adenylate cyclase, comprising administering an effective amount of a compound of claim 7 to a subject in need thereof.

14. A pharmaceutical composition, comprising a compound of claim 7 and a pharmaceutically acceptable carrier.

15. A pharmaceutical composition according to claim 14, which is suitable for enteral, parenteral or oral administration.

* * * * *